(12) United States Patent
Ehara et al.

(10) Patent No.: US 7,087,423 B2
(45) Date of Patent: Aug. 8, 2006

(54) **PROCESS FOR PRODUCING SPORANGIA OF *BACILLUS POPILLIAE***

(75) Inventors: Gaku Ehara, Sakura (JP); Masaharu Kimura, Ichihara (JP); Hideji Nishihashi, Sakura (JP); Tomoko Yokoyama, Chiba (JP); Sachiko Yoshii, Tougane (JP); Hitoshi Nagasaki, Chiba (JP); Masao Tanaka, Chiba (JP); Yasuharu Tomioka, Chiba (JP)

(73) Assignees: Dainippon Ink and Chemicals, Inc., Tokyo (JP); Chiba Prefectural Government, Chiba (JP)

( * ) Notice: Subject to any disclaimer, the term of this patent is extended or adjusted under 35 U.S.C. 154(b) by 0 days.

(21) Appl. No.: 10/743,546

(22) Filed: Dec. 23, 2003

(65) Prior Publication Data

US 2005/0136526 A1    Jun. 23, 2005

(51) Int. Cl.
*C12N 3/00* (2006.01)
*C12N 1/00* (2006.01)
*C12N 1/12* (2006.01)
*A01N 63/00* (2006.01)

(52) U.S. Cl. .................. 435/242; 435/243; 435/252.31; 424/93.46

(58) Field of Classification Search ............. 424/93.46; 435/243, 252.31
See application file for complete search history.

(56) References Cited

U.S. PATENT DOCUMENTS

| 4,824,671 A | 4/1989 | Ellis et al. .................. 424/195 |
| 2005/0123518 A1 * | 6/2005 | Ehara et al. ................ 424/93.4 |

FOREIGN PATENT DOCUMENTS

| JP | 2001-149066 | 6/2001 |
| JP | 2002-355030 | * 12/2002 |

OTHER PUBLICATIONS

Pettersson et al; "Transfer of *Bacillus lentimorbus* and *Bacillus popilliae* to the genus *Paenibacillus* with emended descriptions of *Paenibacillus lentimorbus* comb. Nov. and *Paenibacillus popilliae* comb. Nov." Int'l Journal of Systematic Bacteriology (1999); 49, pp. 531-540.

Fukuhara, T. Konchuu Byourigaku (1991); Insect Pathology, pp. 54-59; with partial English translation.

Haynes et al; "Sporogenicity of Yeast Autolyzates and Casein Hydrolyzates for *Bacillus popilliae* in Liquid Cultures"; J. Invertebrate Pathology (1973); 22, pp. 377-381.

Haynes et al; "Sporulation of *Bacillus popilliae* in Liquid Cultures"; J. Invertebrate Pathology (1972); 19, pp. 125-130.

Co-pending U.S. Appl. No. 10/730,258 filed Dec. 9, 2003; entitled: "Process for Producing Sporangia of *Bacillus popilliae*, Control Agent, and Controlling Method.".

* cited by examiner

*Primary Examiner*—Lynette R. F. Smith
*Assistant Examiner*—Lakia J. Tongue
(74) *Attorney, Agent, or Firm*—Armstrong, Kratz, Quintos, Hanson & Brooks, LLP

(57) ABSTRACT

The present invention provides a process for producing sporangia of *Bacillus popilliae* containing spores and parasporal bodies in large numbers per unit volume of medium. In a process for producing sporangia of *Bacillus popilliae* containing spores and parasporal bodies by culturing *Bacillus popilliae* in a liquid medium containing an adsorbent, the liquid medium contains 0.1–0.7% by weight of proline.

6 Claims, 2 Drawing Sheets

_US 7,087,423 B2_

PROCESS FOR PRODUCING SPORANGIA OF *BACILLUS POPILLIAE*

BACKGROUND OF THE INVENTION

1. Field of the Invention

The present invention relates to a process for producing sporangia of microorganisms belonging to *Bacillus popilliae* containing spores and parasporal bodies useful as a control agent of *Scarabaeidae* insects ("sporangia containing spores and parasporal bodies" may simply be referred to as "sporangia") by culturing *Bacillus popilliae* in liquid medium.

2. Description of the Related Art

The larva of *Scarabaeidae* insects feed on a wide range of plant roots such as those of grasses, agricultural and horticultural crops and trees, and are known to cause considerable damage. Since these larva live underground, it is difficult obtain control effects by spraying agricultural chemicals from the air, and it is difficult to identify the locations where these larva are present. Therefore, it has been necessary to spray large amounts of agricultural chemicals over a wide range to enable the chemicals to penetrate into the ground, and since there are concerns over detrimental effects on both the natural environment and people, a more effective control method is desired.

Microorganisms belonging to *Bacillus popilliae* are known to parasitically cause milky disease in the larva of *Scarabaeidae* insects, and eventually cause their death. Consequently, attempts have long been made to use the sporangia of these microorganisms to control *Scarabaeidae* insects on which agricultural chemicals have little effect.

For example, an example of a production process is described in Japanese Unexamined Patent Application, First Publication No. 2001-149066 in which a sporangia formation rate (ratio of number of sporangia to number of microbial cells) of 4.8% is obtained by culturing *Bacillus popilliae* in solid medium containing 0.05–0.5% by weight of activated carbon. However, culturing methods using solid medium have the problem of low productivity.

Various studies have been conducted on culturing methods using liquid medium in order to solve this problem of the aforementioned culturing method using solid medium. For example, Haynes, et al. reported an example of attempting to culture *Bacillus popilliae* NRRL B-2390S in liquid medium containing 0.5% peptone, 1.5% yeast extract, 0.3% dipotassium hydrogenphosphate, 0.1% glucose and 1% activated carbon (Journal of Invertebrate Pathology, Vol. 22, p. 377–381, 1973). However, only a maximum of $2.06 \times 10^7$ sporangia per 1 ml of liquid culture were obtained, thus resulting in the problem the concentration of sporangia being too low to achieve higher productivity.

In addition, Haynes, et al. also reported that $3.1 \times 10^7$ sporangia per 1 ml of liquid culture were obtained by culturing mature cells of *Bacillus popilliae* NRRL B-2309S in the late logarithmic increase stage in liquid medium containing 0.5% peptone (tryptone), 1.5% yeast extract, 0.3% dipotassium hydrogenphosphate, 0.1% glucose and 1% activated carbon (Journal of Invertebrate Pathology, Vol. 19, p. 125–130, 1972). However, this culturing method has a long culturing time, taking roughly two weeks.

Moreover, an example of having obtained $1 \times 10^9$ sporangia per 1 ml of liquid culture by culturing in liquid medium containing 1% soluble starch, 0.1% trehalose, 0.5% yeast extract, 0.3% dipotassium hydrogenphosphate and 0.1% calcium carbonate is indicated in U.S. Pat. No. 4,824,671. However, there were no parasporal bodies present in the sporangia, and as a result, the rate of infection with milky disease when sporangia were sprayed at the rate of $2.0 \times 10^{12}$ sporangia per 1 kg of soil and allowed to be orally ingested by larva of *Scarabaeidae* insects was 47.50% after the passage of 7 weeks, indicating weak insecticidal effects on larva of *Scarabaeidae* insects even when compared with sporangia containing parasporal bodies formed within the bodies of the larva.

BRIEF SUMMARY OF THE INVENTION

The object of the present invention is to provide a process for producing sporangia of microorganisms belonging to *Bacillus popilliae* of which a large number are produced per unit volume of medium.

In order to solve the aforementioned problems, the present invention provides a process for producing sporangia of microorganisms belonging to *Bacillus popilliae* containing spores and parasporal bodies by culturing *Bacillus popilliae* in liquid medium containing an adsorbent and 0.1–0.7% by weight of proline.

According to the production process of the present invention, $5 \times 10^7$ sporangia or more of *Bacillus popilliae* containing spores and parasporal bodies can be produced per 1 ml of liquid culture and at a high sporangia formation rate of 6–50% by liquid culturing for about 5–10 days. In addition, the number of sporangia produced per unit volume of medium can be further increased by adding pyruvic acid to the liquid medium.

DETAILED DESCRIPTION OF THE PREFERRED EMBODIMENTS

Figure 1:
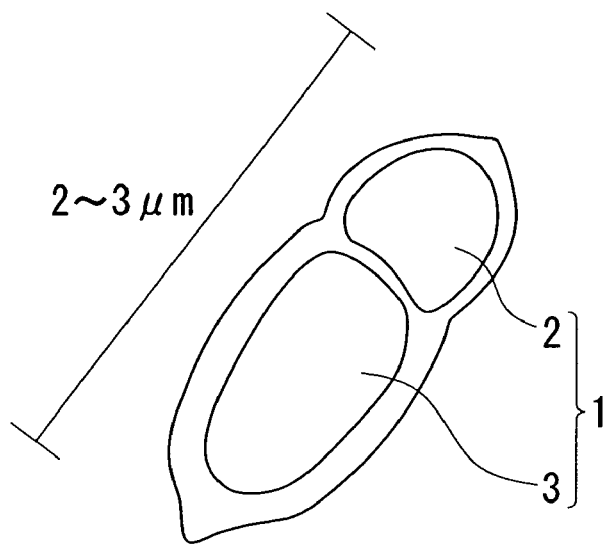
FIG. 1 is a schematic drawing showing a sporangium of *Bacillus popilliae* containing a spore and a parasporal body.

According to Bergey's Manual of Determinative Bacteriology, Eighth Edition, the bacteriological properties of the microorganisms belonging to *Bacillus popilliae* used in the present invention consist of morphological properties including being Gram negative bacilli having a length of 1.3–5.2 μm and width of 0.5–0.8 μm, a growth temperature of 20–35° C., and the sporangium 1 having a spore 3 and parasporal body 2 inside as shown in the schematic drawing of FIG. 1. However, it has been proposed, based on the theoretical opinions of Pettersson, et al. (Int. J. Syst. Bacteriol., Vol. 49, p. 531–540, 1999), that *Bacillus popilliae* should be reclassified as *Paenibacillus popilliae*. In addition, Rippere, et al. (Int. J. Syst. Bacteriol., Vol. 48, p. 395–402, 1998) and Harrison, et al. (J. Invertebr. Pathol., Vol. 76, p. 169–175, 2000) have proposed that the milky disease pathogens of *Bacillus popilliae* and *Bacillus lentimorbus* be classified at the DNA level since they cannot be clearly distinguished on the basis of only the presence or absence of parasporal bodies and the presence or absence of growth in 2% salt-containing medium, which had been used to distinguish the two species in the past. Since their classification is not clearly defined at present, the microorganisms belonging to *Bacillus popilliae* in the present invention are to include microorganisms belonging to *Paenibacillus popilliae* and microorganisms belonging to *Paenibacillus lentimorbus*.

The liquid medium used in the present invention contains an adsorbent for the purpose of removing substances that inhibit the growth of *Bacillus popilliae*. Examples of said adsorbent used for this purpose include activated carbon, adsorbent resin, allophosite and molecular sieve, and activated carbon is particularly preferable. Although the activated carbon used for the adsorbent may be in the form of a powder, granules or a sheet and so forth, powdered activated carbon is particularly preferable because it has the highest decomposition or adsorption ability per unit weight.

Adsorbent resin refers to a porous polymer that has adsorbent properties, examples of which include crosslinked porous polymers molded into granules which function as a synthetic resin capable of efficiently adsorbing growth inhibiting substances in aqueous solution due to a microporous structure that extends inside the granules. Examples of adsorbent resins include the aromatic synthetic resin adsorbents manufactured by Mitsubishi Chemical under the trade names of Diaion HP20, Diaion HP21, Sepabeads SP825, Sepabeads SP850, Sepabeads SP70 and Sepabeads SP700, the substituted aromatic synthetic resin adsorbent manufactured by Mitsubishi Chemical under the trade name of Sepabeads SP207, and the acrylic synthetic resin adsorbent also manufactured by Mitsubishi Chemical under the trade name of Diaion HP2MG.

The content of adsorbent in the liquid medium used in the present invention is preferably 0.05–5% by weight of the liquid medium. By making the content of adsorbent in the liquid medium 0.05% by weight or more, adsorption and elimination effects on substances that inhibit microorganism growth tend to be adequately demonstrated, and by making the content of adsorbent in the liquid medium 5% by weight or less, the adsorption of nutrient sources required for growth of the microorganisms tends to be minimized, which is preferable since a high level of microbial growth promotional effects for *Bacillus popilliae* are demonstrated within the aforementioned range.

The proline content in the liquid medium used in the present invention is preferably 0.1–0.7% by weight, and particularly preferably 0.2–0.6% by weight, of the liquid medium. If the content of proline in the liquid medium is less than 0.1% by weight or if it exceeds 0.7% by weight, in addition to lowering microbial growth promotion effects, the number of sporangia formed per unit volume of medium also decreases.

Medium should be used for the liquid medium used in the present invention that contains proline and adsorbent at the aforementioned content ratios in a known liquid medium used to culture *Bacillus popilliae*.

Examples of components contained in such known liquid media include nitrogen sources, carbon sources and inorganic salts.

Examples of nitrogen sources include inorganic nitrogen sources normally used for culturing microorganisms such as ammonia, nitric acid and salts thereof, and organic nitrogen sources such as peptones, meat extract, fish extract, lactoalbumin hydrolyzates and yeast extract. Among these, peptones, lactoalbumin hydrolyzates and yeast extract are particularly preferable. The content of nitrogen sources in the liquid medium used in the present invention is preferably 0.001–5% by weight, and particularly preferably 0.2–4% by weight.

Although various amino acids are contained in the aforementioned nitrogen sources, and proline is included in these amino acids, the proline content is extremely low. In the production process of the present invention, proline is added separately to a known liquid medium so that the ratio of proline to total amino acids in the liquid medium is preferably 10–65% by weight, and particularly preferably 25–50% by weight.

The aforementioned total amino acids refer to 16 types of free amino acids composed of alanine, arginine, aspartic acid, glutamic acid, glycine, isoleucine, leucine, lysine, methionine, phenylalanine, proline, serine, threonine, histidine, tyrosine and valine that are known to be contained in nitrogen sources such as peptones and yeast extract ordinarily used as components of liquid media. The total amount of these 16 types of free amino acids is frequently used to roughly indicate the total amount of free amino acids contained in peptones, yeast extract and so forth.

Examples of carbon sources that can be used as carbon sources in the present invention include sugars such as starches, trehalose and sucrose, and agricultural waste products such as waste honey, starch degradation products and cheese whey. The content of these carbon sources is preferably 0.001–5% by weight of the liquid medium. However, although glucose is suited for growth of *Bacillus popilliae*, since it tends to inhibit the formation of sporangia containing spores and parasporal bodies, the concentration of glucose contained in the liquid medium is preferably 0.01% by weight or less of the liquid medium.

Examples of inorganic salts include potassium chloride, sodium chloride, calcium chloride, sodium carbonate and phosphates normally used for culturing microorganisms, with phosphates being preferable, potassium dihydrogenphosphate, dipotassium hydrogenphosphate and disodium hydrogenphosphate being particularly preferable. The content of inorganic salt is preferably 1% by weight or less of the liquid medium.

In addition to these components, other known additives may also be used such as pH adjusters within a range that does not impair the effects of the present invention.

Among the components of the liquid medium described above, an example of a liquid medium preferable for use in the production process of the present invention is shown in Table 1.

TABLE 1

| Liquid Medium | Medium components (contents) or pH |
|---|---|
| Example 1 | Proline (0.1–0.7 wt %)<br>Adsorbent (0.05–5 wt %)<br>Peptone, yeast extract and lactoalbumin hydrolyzate (0.001–5 wt %)<br>Trehalose (0.001–5 wt %)<br>Water<br>pH (6.5–8.5) |
| Example 2 | Proline (0.1–0.7 wt %)<br>Adsorbent (0.05–5 wt %)<br>Peptone and yeast extract (0.001–5 wt %)<br>Trehalose (0.001–5 wt %)<br>Water<br>pH (6.5–8.5) |

In addition, pyruvic acid is also preferably added to the liquid medium containing proline and adsorbent used in the present invention. The addition of pyruvic acid to the liquid medium further promotes growth of *Bacillus popilliae*, while also further increasing the number of sporangia containing spores and parasporal bodies produced per unit volume of medium. Furthermore, the pyruvic acid used in the present invention also includes physiologically acceptable salts thereof. Specific examples of physiologically acceptable salts of pyruvic acid include sodium pyruvate and potassium pyruvate.

The content of pyruvic acid in the liquid medium in the case of adding pyruvic acid to the liquid medium is preferably 0.01–0.5% by weight, and particularly preferably 0.03–0.3% by weight, of the liquid medium. By making the content of pyruvic acid in the liquid medium 0.01–0.5% by weight, a high level of growth promotional effects can be exhibited for Bacillus popilliae, and the number of the aforementioned sporangia can be increased per unit volume of medium.

The suitable culturing temperature for the growth of Bacillus popilliae is 25–32° C. In addition, the pH of the liquid medium is preferably 6.5–8.5, and particularly preferably 7–8. Examples of methods for adjusting the pH of the liquid medium include the addition of various buffers, the addition of routinely used acids such as hydrochloric acid or sulfuric acid, and the addition of routinely used bases such as sodium hydroxide, potassium hydroxide or ammonia.

Liquid culturing may be carried out by any method, examples of which include batch culturing, continuous culturing, semi-batch culturing and feeding culturing. Although culturing time varies according to the culturing method, culture temperature, culture pH and number of inoculated microorganisms, it is normally 5–10 days in the case of batch culturing.

Following completion of culturing, sporangia containing spores and parasporal bodies are recovered from the culture. This recovery should be carried out by separating microbial cells containing said sporangia from the culture by centrifugation, filtration or other typical separation method. At this time, a washing procedure may be added using water or buffer as necessary.

According to the production process of the present invention, sporangia of Bacillus popilliae can be produced at a sporangia formation rate of 6–50%, and $5 \times 10^7$ to $1 \times 10^9$ of said sporangia can be produced per 1 ml of liquid culture.

The sporangia of Bacillus popilliae containing spores and parasporal bodies obtained from the production process of the present invention are useful as a control agent for Scarabaeidae insects by demonstrating control effects such as insecticidal activity on Scarabaeidae insects and growth inhibition on their larva.

Examples of microorganisms belonging to Bacillus popilliae that exhibit growth inhibitory or insecticidal activity against larva of Scarabaeidae insects include the bacterial species of Bacillus popilliae Semadara: FERM BP-8068, Bacillus popilliae var. popilliae Mame: FERM BP-8069, Bacillus popilliae var. popilliae Hime: FERM P-17660, Bacillus popilliae var. popilliae Sakura: FERM P-17662, Bacillus popilliae Dutky: ATCC No. 14706, and Bacillus popilliae subsp. melolonthae. Furthermore, Bacillus popilliae Semadara was deposited at the National Institute of Bioscience and Human-Technology, Agency of Industrial Science and Technology (currently the International Patent Organism Depository, National Institute of Advanced Industrial Science and Technology) on May 21, 1998 under the accession no. FERM P-16818, was transferred to international deposition based on the Budapest Treaty on Jun. 10, 2002, and assigned the accession no. FERM BP-8068. In addition, Bacillus popilliae var. popilliae Mame was deposited at the National Institute of Bioscience and Human-Technology, Agency of Industrial Science and Technology (currently the International Patent Organism Depository, National Institute of Advanced Industrial Science and Technology) on Nov. 25, 1999 under the accession no. FERM P-17661, was transferred to international deposition based on the Budapest Treaty on Jun. 10, 2002, and assigned the accession no. FERM BP-8069.

On the other hand, examples of Scarabaeidae insects that can be controlled include Anomala cuprea, Blitopertha orientalis, Popillia japonica, Phyllopertha diversa, Adoretus tenuimaculatus and Anomala rufocuprea.

Sporangia of Bacillus popilliae containing spores and parasporal bodies produced according to the production process of the present invention may be used as a control agent for Scarabaeidae insects directly in the form of a liquid in which they are suspended. Alternatively, the sporangia may be dried and sprayed in the form of a powder. In addition, the sporangia may be dried followed by spraying onto the soil as a suspension with water or buffer. However, said sporangia are normally formulated with commonly used additives used in agricultural chemicals using ordinary microbial agricultural chemical production methods, and then preferably applied in the form of a control agent for Scarabaeidae insects. In addition, the sporangia of Bacillus popilliae containing spores and parasporal bodies obtained according to the production process of the present invention can also be used by mixing with other microbial preparations. Although there are no particular restrictions on the content ratio of sporangia of Bacillus popilliae containing spores and parasporal bodies contained in the aforementioned control agent provided it is within a range that demonstrates control effects on Scarabaeidae insects, in the case of, for example, a water-dispersible powder or emulsion at the time of application, it is preferably formulated so as to contain $1 \times 10^9$ to $1 \times 10^{13}$ sporangia per 1 liter of control agent, while in the case of a powder or granules, it is preferably formulated so as to contain $1 \times 10^8$ to $1 \times 10^{12}$ sporangia per 1 gram of control agent.

The method for applying the control agent of the present invention is suitably selected according to the preparation form, target crop and so forth, examples of which include ground-level liquid spraying, ground-level solid spraying, aerial liquid spraying, aerial solid spraying, indoor application, soil mixing and soil perfusion. In addition, the control agent of the present invention can also be applied by mixing with other chemicals such as insecticides, nematocides, miticides, herbicides, bactericides, plant growth regulators, fertilizers and soil improvers (such as peat, humus and polyvinyl alcohol-based materials), or can be applied alternately or simultaneously with other chemicals without being mixed with them.

Although the applied amount of the aforementioned control agent cannot be specified unconditionally since it varies according to the type of Scarabaeidae insect, type of applied plant, preparation form and so forth, in the case of ground-level spraying, for example, the applied amount of sporangia of Bacillus popilliae containing spores and parasporal bodies of the present invention is $10^{10}$–$10^{15}$ sporangia/are, and preferably $10^{11}$–$10^{14}$ sporangia/are.

EXAMPLES

The following provides a more detailed explanation of the present invention through its examples and test examples.

Reference Example 1

The free amino acid contents of the peptone, yeast extract and lactoalbumin hydrolyzate added to the liquid media of each example were measured by the post column method described below using orthophthalaldehyde (OPA).

(1) Sample Preparation

Mixed amino acid standard H (Wako Pure Chemical Industries, containing 2.5 mmol/l of each amino acid) used as the reference sample was diluted five-fold with hydrochloric acid having a concentration of 0.02 mol/l and filtered with a filter having a pore size of 0.2 μm to prepare the reference sample solution.

Measurement samples were prepared by preparing 1.0% by weight solutions of Polypeptone S (Nippon Pharmaceutical) or Tryptone (Difco) for the peptone, 1.0% by weight solutions of yeast extract manufactured by Oxoid or Difco for the yeast extract, and 1.0% by weight solutions of lactoalbumin hydrolyzate (Wako Pure Chemical Industries), followed by diluting these solutions two-fold with 10% by weight aqueous trichloroacetic acid solution, stirring well and centrifuging to remove any insoluble precipitates. Subsequently, the supernatant was filtered with a filter having a pore size of 0.2 μm to prepare the measurement sample solutions.

(2) Analysis

10 μl aliquots of the reference sample solution and measurement sample solutions were injected into a high-performance liquid chromatograph to analyze the amino acids. Furthermore, amino acid analyses were carried out using the Hitachi "LaChrom" Amino Acid Auto Analyzer. Furthermore, the compositions of the OPA labeling reaction solutions and eluates used in the amino acid analyses are shown in Tables 2 and 3, respectively.

TABLE 2

| Composition of reaction solution for OPA labeling | R1 | R2 | R3 |
|---|---|---|---|
| Boric acid | | 21.6 g | 21.6 g |
| Sodium hydroxide | 24.0 g | | |
| 25% Brij-35 solution | | 4.0 ml | 4.0 ml |
| o-phthalaldehyde/methanol | | | 800 mg/ 10 ml |
| 2-mercaptoethanol | | | 2.0 ml |
| 5% sodium hypochlorite solution | | 150.0 μl | |
| Distilled Water | Remainder | Remainder | Remainder |
| Total volume | 1,000 ml | 1,000 ml | 1,000 ml |

TABLE 3

| Eluate | A | B | C |
|---|---|---|---|
| Sodium citrate 2H$_2$O | 8.14 g | 26.67 g | |
| Sodium chloride | 7.07 g | 54.35 g | |
| Citric acid H$_2$O | 20.00 g | 6.10 g | |
| Sodium hydroxide | | | 8.0 g |
| Ethanol | 110 ml | | |
| Caprylic acid | 0.1 ml | 0.1 ml | 0.1 ml |
| Distilled Water | Remainder | Remainder | Remainder |
| Total | 1,000 ml | 1,000 ml | 1,000 ml |

Reagents manufactured by Wako Pure Chemical Industries were used for all reagents, and amino acid analytical grade reagents were used for the sodium citrate 2H$_2$O, citric acid H$_2$O and caprylic acid, while guaranteed reagents were used for all others. The concentrations of proline and total amino acids contained in each of the measurement sample solutions were calculated by converting from the peak areas obtained from the reference sample solution and each measurement sample solution, and those concentrations are shown in Table 4.

TABLE 4

| | Peptone | | Yeast extract | | Lacto-albumin hydrolyzate |
|---|---|---|---|---|---|
| | Poly-peptone S | Tryptone | Oxoid | Difco | |
| Proline concentration (wt %) | 0.000 | 0.124 | 0.419 | 0.285 | 0.103 |
| Total amino acid concentration (wt %) | 17.878 | 21.653 | 36.668 | 31.452 | 27.369 |

Preparation Example 1

5 g of L-proline as added amino acid (guaranteed reagent, Wako Pure Chemical Industries), 5 g of peptone ("Polypeptone S", Nippon Pharmaceutical), 5 g of yeast extract (Oxoid) and 5 g of trehalose dihydrate (guaranteed reagent, Wako Pure Chemical Industries were added to a beaker containing 700 g of distilled water and mixed. Moreover, aqueous potassium hydroxide solution having a concentration of 5 mol/l was added while stirring to adjust the pH to 7.6. Moreover, distilled water was added to bring to a final weight of 850 g. This liquid medium was then transferred to a fermentation tank equipped with a pH electrode (B. E. Marubishi) and sterilized by autoclaving for 60 minutes at 121° C.

Next, 3 g of activated carbon powder (guaranteed reagent, Wako Pure Chemical Industries) were placed in a flask followed by the addition of distilled water to bring to a final weight of 100 g to prepare an activated carbon dispersion. In addition, 1 g of antifoaming agent (Disfoam CA-123, NOF) was placed in a flask followed by the addition of distilled water to bring to a final weight of 50 g to prepare an antifoaming agent liquid. The activated carbon dispersion and antifoaming agent liquid were sterilized followed by their aseptic addition to the fermentation tank to prepare liquid medium (A).

Comparative Preparation Example 1

Liquid medium (B-1) was obtained in the same manner as Preparation Example 1 with the exception of not adding activated carbon powder in Preparation Example 1.

Comparative Preparation Example 2

Liquid medium (B-2) was obtained in the same manner as Preparation Example 1 with the exception of not adding L-proline in Preparation Example 1.

Comparative Preparation Example 3

Liquid medium (B-3) was obtained in the same manner as Preparation Example 1 with the exception of adding 5 g of L-alanine (guaranteed reagent, Wako Pure Chemical Industries) instead of the L-proline in Preparation Example 1.

TABLE 5

| Medium Name | | Medium A | Medium B-1 | Medium B-2 | Medium B-3 |
|---|---|---|---|---|---|
| Medium compo- nents | Added amino acid | L-proline 5 g | L-proline 5 g | — | L-alanine 5 g |
| | Activated carbon | 3 g | — | 3 g | 3 g |
| | Peptone | 5 g | 5 g | 5 g | 5 g |
| | Yeast extract | 5 g | 5 g | 5 g | 5 g |
| | Trehalose dihydrate | 5 g | 5 g | 5 g | 5 g |
| | Antifoaming agent | 1 g | 1 g | 1 g | 1 g |
| | Distilled water | Remainder | Remainder | Remainder | Remainder |
| | Total Amount | 1,000 g | 1,000 g | 1,000 g | 1,000 g |

Comparative Preparation Example 4

Liquid medium (B-4) was obtained by placing 80 g of distilled water in a flask, mixing in 0.5 g of peptone ("Tryptone", Difco), 0.5 g of yeast extract (Oxoid) and 0.3 g of dipotassium hydrogenphosphate (guaranteed reagent, Wako Pure Chemical Industries), 0.1 g of glucose (guaranteed reagent, Wako Pure Chemical Industries) and 1.0 g of activated carbon powder (guaranteed reagent, Wako Pure Chemical Industries), and adding distilled water to bring to a final weight of 100 g followed by sterilizing in an autoclave for 20 minutes at 121° C.

TABLE 6

| | Medium Name | B-4 |
|---|---|---|
| Medium Components | Activated carbon | 1.0 g |
| | Tryptone | 0.5 g |
| | Yeast extract | 1.5 g |
| | Glucose | 0.1 g |
| | Dipotassium hydrogenphosphate | 0.3 g |
| | Distilled water | Remainder |
| | Total Amount | 100 g |

Example 1

Sporangia of *Bacillus popilliae Semadara* (FERM BP-8068), *Bacillus popilliae* var. *popilliae Sakura* (FERM P-17662) and *Bacillus popilliae* var. *popilliae Mame* (FERM BP-8069) were cultured in advance by a known method of solid culturing described in Japanese Unexamined Patent Application, First Publication No. 2001-149066. Moreover, each of the microorganisms were collected aseptically, and the number of sporangia containing spores and parasporal bodies in 1 ml of distilled water was adjusted to $1\times10^9$ sporangia by measuring by direct microscopic examination to prepare sporangia liquids.

1 ml aliquots of the sporangia liquid of each strain were transferred to plastic tubes followed by heat treatment for 20 minutes at 70° C. using a heating block. 1 ml of each sporangia liquid was inoculated into liquid medium (A) in the aforementioned fermentation tank (B. E. Marubishi) followed by culturing for 7 days under controlled conditions of aeration of 1 vvm, 30° C. and pH 7.6 while stirring the liquid medium by rotating the stirrer provided with the fermentation tank at 150 rpm.

Following completion of culturing, the numbers of sporangia and microbial cells per unit volume in the liquid cultures were measured by direct microscopic examination (Eclipse E600, Nikon, magnification: 3800×) followed by calculation of the sporangia formation rate relative to the number of microorganisms. The numbers of sporangia per 1 ml of liquid culture and sporangia formation rates are shown in Tables 7 through 9.

Comparative Examples 1–3

With the exception of using liquid media (B-1), (B-2) and (B-3), respectively, in place of liquid medium (A) in Example 1, culturing was carried out in the same manner as Example 1, and the numbers of sporangia containing spores and parasporal bodies as well as the numbers of microbial cells per unit volume in the liquid cultures were measured followed by calculation of the sporangia formation rates. The numbers of sporangia and sporangia formation rates per 1 ml of liquid culture are shown in Tables 7 through 9.

Comparative Example 4

With the exception of using liquid medium (B-4) in place of liquid medium (A), and setting the rotation condition of stirrer to be 100 rpm in Example 1, culturing was carried out in the same manner as Example 1, and the number of sporangia containing spores and parasporal bodies as well as the number of microbial cells per unit volume in the liquid culture were measured followed by calculation of the sporangia formation rate. The number of sporangia and sporangia formation rate per 1 ml of liquid culture are shown in Tables 7 through 9.

TABLE 7

Culture of *Bacillus popilliae Semadara*

| Medium Name | Proline concentration in liquid medium (wt %) | Ratio of proline to total amino acids (wt %) | No. of sporangia (sporangia/ml) | Sporangia formation rate (%) |
|---|---|---|---|---|
| A | 0.502 | 64.977 | $1.1 \times 10^8$ | 6.2 |
| B-1 | 0.502 | 64.977 | $<1.0 \times 10^4$ | 0 |
| B-2 | 0.002 | 0.768 | $<1.0 \times 10^4$ | 0 |
| B-3 | 0.002 | 0.768 | $<1.0 \times 10^4$ | 0 |
| B-4 | 0.007 | 1.049 | $<1.0 \times 10^4$ | 0 |

TABLE 8

Culture of *Bacillus popilliae* var. *popilliae Sakura*

| Medium Name | Proline concentration in liquid medium (wt %) | Ratio of proline to total amino acids (wt %) | No. of sporangia (sporangia/ml) | Sporangia formation rate (%) |
|---|---|---|---|---|
| A | 0.502 | 64.977 | $1.1 \times 10^8$ | 6.9 |
| B-1 | 0.502 | 64.977 | $<1.0 \times 10^4$ | 0 |

TABLE 8-continued Culture of *Bacillus popilliae* var. *popilliae Sakura*

| Medium Name | Proline concentration in liquid medium (wt %) | Ratio of proline to total amino acids (wt %) | No. of sporangia (sporangia/ml) | Sporangia formation rate (%) |
|---|---|---|---|---|
| B-2 | 0.002 | 0.768 | <1.0 × 10$^4$ | 0 |
| B-3 | 0.002 | 0.768 | <1.0 × 10$^4$ | 0 |
| B-4 | 0.007 | 1.049 | <1.0 × 10$^4$ | 0 |

TABLE 9

Culture of *Bacillus popilliae* var. *popilliae Mame*

| Medium Name | Proline concentration in liquid medium (wt %) | Ratio of proline to total amino acids (wt %) | No. of sporangia (sporangia/ml) | Sporangia formation rate (%) |
|---|---|---|---|---|
| A | 0.502 | 64.977 | 1.1 × 10$^8$ | 7.1 |
| B-1 | 0.502 | 64.977 | <1.0 × 10$^4$ | 0 |
| B-2 | 0.002 | 0.768 | <1.0 × 10$^4$ | 0 |
| B-3 | 0.002 | 0.768 | <1.0 × 10$^4$ | 0 |
| B-4 | 0.007 | 1.049 | <1.0 × 10$^4$ | 0 |

Based on the results of Tables 7 through 9, sporangia are only obtained in liquid media to which has been added adsorbent and proline, and said sporangia were confirmed by microscopic observation to contain one spore and one parasporal body.

Preparation Example 2

0.1 g of L-proline (guaranteed reagent, Wako Pure Chemical Industries), 7.5 g of peptone ("Polypeptone S", Nippon Pharmaceutical), 7.5 g of yeast extract (Oxoid), 5 g of lactoalbumin hydrolyzate (guaranteed reagent, Wako Pure Chemical Industries) and 5 g of trehalose dihydrate (guaranteed reagent, Wako Pure Chemical Industries) were added to a beaker containing 700 g of distilled water and mixed. After adjusting the pH to 7.6 by adding aqueous potassium hydroxide solution having a concentration of 5 mol/l while stirring, distilled water was added to bring to a final weight of 850 g. This was then transferred to a fermentation tank equipped with a pH electrode (B. E. Marubishi) and sterilized by autoclaving for 60 minutes at 121° C.

Next, 3 g of activated carbon powder (guaranteed reagent, Wako Pure Chemical Industries) were added to a flask followed by the addition of distilled water to bring to a final weight of 100 g to prepare an activated carbon dispersion. In addition, 1 g of antifoaming agent (Disfoam CA-123, NOF) was added to a flask followed by the addition of distilled water to bring to a final weight of 50 g to prepare an antifoaming agent liquid. The activated carbon dispersion and antifoaming agent liquid were sterilized followed by their aseptic addition to each fermentation tank to obtain medium (C-1).

Preparation Examples 3 and 4

Liquid media (C-2) and (C-3) were respectively prepared in the same manner as Preparation Example 2 with the exception of changing the amount of L-proline added to 0.2 g and 0.5 g, respectively, in Preparation Example 2.

Comparative Preparation Example 5

Liquid medium (D-1) was prepared in the same manner as Preparation Example 2 with the exception of not adding L-proline in Preparation Example 2.

Comparative Preparation Example 6

Liquid medium (D-2) was prepared in the same manner as Preparation Example 2 with the exception of changing the amount of L-proline added to 0.8 g in Preparation Example 2.

TABLE 10

| | Medium Name | D-1 | C-1 | C-2 | C-3 | D-2 |
|---|---|---|---|---|---|---|
| Medium components | L-proline | — | 0.1 g | 0.2 g | 0.5 g | 0.8 g |
| | Activated carbon | 3 g | 3 g | 3 g | 3 g | 3 g |
| | Peptone | 7.5 g | 7.5 g | 7.5 g | 7.5 g | 7.5 g |
| | Yeast extract | 7.5 g | 7.5 g | 7.5 g | 7.5 g | 7.5 g |
| | Lactoalbumin hydrolyzate | 5 g | 5 g | 5 g | 5 g | 5 g |
| | Trehalose dihydrate | 5 g | 5 g | 5 g | 5 g | 5 g |
| | Antifoaming agent | 1 g | 1 g | 1 g | 1 g | 1 g |
| | Distilled water | Remainder | Remainder | Remainder | Remainder | Remainder |
| | Total Amount | 1,000 g | 1,000 g | 1,000 g | 1,000 g | 1,000 g |

Examples 2–4 and Comparative Examples 5–6

Sporangia of *Bacillus popilliae Semadara* (FERM BP-8068) were cultured in advance by a known method of solid culturing described in Japanese Unexamined Patent Application, First Publication No. 2001-149066. Moreover, the microorganisms were collected aseptically, and the number of sporangia containing spores and parasporal bodies in 1 ml of distilled water was adjusted to 1×10$^9$ sporangia by measuring by direct microscopic examination to prepare a sporangia liquid.

1 ml aliquots of the sporangia liquid were transferred to plastic tubes followed by heat treatment for 20 minutes at 70° C. using a heating block. 1 ml each of sporangia liquid was inoculated into liquid media (C-1) through (C-3) and liquid media (D-1) through (D-2) followed by culturing for 7 days under the same conditions as Example 1.

Following completion of culturing, the numbers of sporangia and microbial cells per unit volume in the liquid cultures were measured by direct microscopic examination followed by calculation of the sporangia formation rates. The numbers of sporangia per 1 ml of liquid culture and sporangia formation rates are shown in Table 11.

TABLE 11

| Medium Name | L-proline content in liquid culture (wt %) | Ratio of L-proline to total amino acids (wt %) | No. of microbial cells (cells/ml) | No. of sporangia (sporangia/ml) | Sporangia formation rate (%) |
|---|---|---|---|---|---|
| D-1 | 0.004 | 0.670 | $5.6 \times 10^8$ | $<1.0 \times 10^4$ | 0 |
| C-1 | 0.104 | 16.048 | $1.5 \times 10^9$ | $8.2 \times 10^7$ | 5.5 |
| C-2 | 0.204 | 27.302 | $1.1 \times 10^9$ | $1.6 \times 10^8$ | 10.6 |
| C-3 | 0.504 | 48.154 | $1.8 \times 10^9$ | $1.8 \times 10^8$ | 10.0 |
| D-2 | 0.804 | 59.710 | $3.5 \times 10^8$ | $<1.7 \times 10^7$ | 0 |

Figure 2:
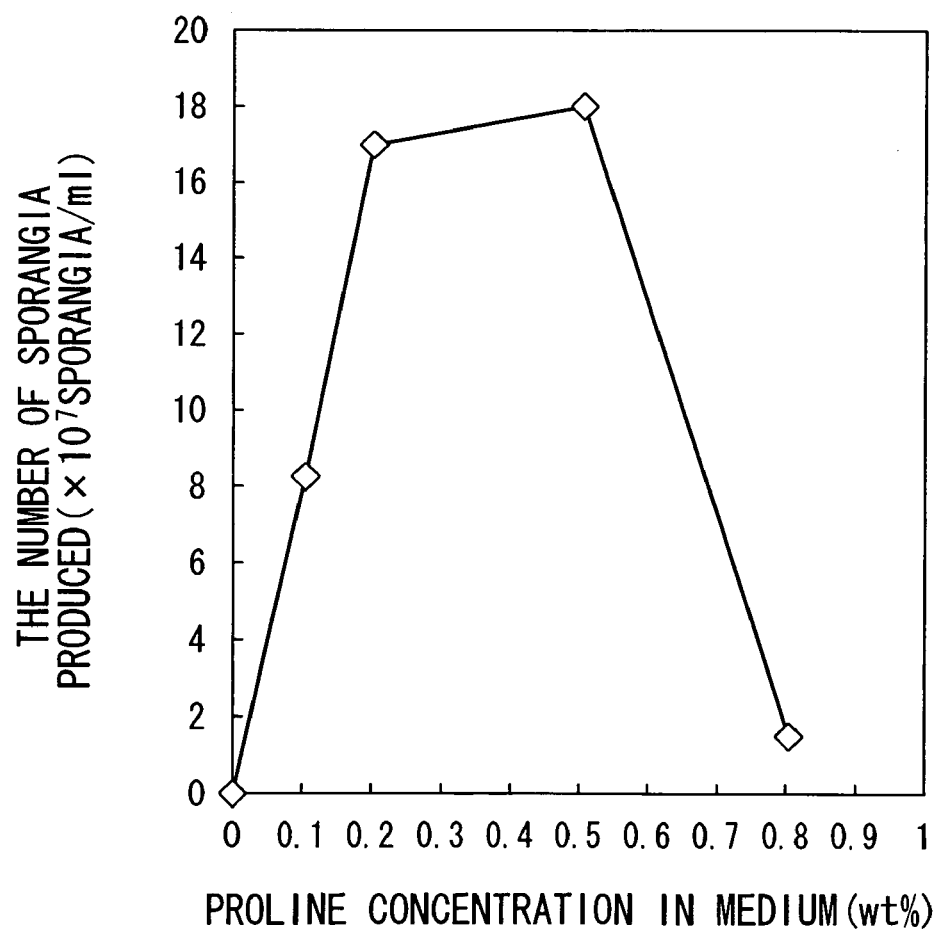
FIG. 2 is a graph showing the relationship between the number of sporangia containing spores and parasporal bodies produced versus proline concentration in liquid media in Examples 2–4 and Comparative Examples 5–6.

One spore and one parasporal body were contained in the sporangia obtained in Examples 2–4 using media (C-1) through (C-3). In addition, the relationship between proline concentration in the liquid medium and sporangia formation rate is shown in FIG. 2 based on results shown in Table 11. It can be seen from FIG. 2 that the optimum proline concentration range is within the range of 0.1–0.7% by weight.

Preparation Example 5

5 g of L-proline (guaranteed reagent, Wako Pure Chemical Industries), 1 g of sodium pyruvate (guaranteed reagent, Wako Pure Chemical Industries), 7.5 g of peptone ("Polypeptone S", Nippon Pharmaceutical), 7.5 g of yeast extract (Oxoid), 5 g of lactoalbumin hydrolyzate (Wako Pure Chemical Industries) and 5 g of trehalose dehydrate (guaranteed reagent, Wako Pure Chemical Industries) were added to a beaker containing 700 g of distilled water and mixed. After adjusting the pH to 7.6 by adding aqueous sodium hydroxide solution having a concentration of 4 mol/l while stirring, distilled water was added to bring to a final weight of 850 g. This was then transferred to a fermentation tank equipped with a pH electrode (B. E. Marubishi) and sterilized by autoclaving for 50 minutes at 121° C.

Next, 2.5 g of activated carbon powder (guaranteed reagent, Wako Pure Chemical Industries) were placed in a flask followed by the addition of distilled water to bring to a final weight of 100 g to prepare an activated carbon dispersion. In addition, 1 g of antifoaming agent (Disfoam CA-123, NOF) was placed in a flask followed by the addition of distilled water to bring to a final weight of 50 g to prepare an antifoaming agent liquid. The activated carbon dispersion and antifoaming agent liquid were sterilized followed by their aseptic addition to the fermentation tank to prepare liquid medium (E-1).

Preparation Example 6

With the exception of using 2.5 g of sodium pyruvate added in Preparation Example 6, liquid medium (E-2) was obtained in the same manner as Preparation Example 6.

Preparation Example 7

Liquid medium (F) was obtained in the same manner as Preparation Example 6 with the exception of not adding L-proline in Preparation Example 6.

TABLE 12

| Medium Name | | E-1 | E-2 | F |
|---|---|---|---|---|
| Medium components | L-proline | 5 g | 5 g | — |
| | Sodium pyruvate | 1 g | 2.5 g | 1 g |
| | Activated carbon | 2.5 g | 2.5 g | 2.5 g |
| | Peptone | 7.5 g | 7.5 g | 7.5 g |
| | Yeast extract | 7.5 g | 7.5 g | 7.5 g |
| | Lactoalbumin hydrolyzate | 5 g | 5 g | 5 g |
| | Trehalose dihydrate | 5 g | 5 g | 5 g |
| | Antifoaming agent | 1 g | 1 g | 1 g |
| | Distilled water | Remainder | Remainder | Remainder |
| | Total Amount | 1,000 g | 1,000 g | 1,000 g |

Examples 5–6 and Comparative Example 7

Using *Bacillus popilliae Semadara* for the inoculating microorganisms in the same manner as Example 2, 1 ml aliquots were aseptically inoculated into liquidmedia (E-1) through (E-2) and liquid medium (F), after which culturing was started in the aforementioned fermentation tank (B. E. Marubishi). The culturing conditions consisted of a temperature of 29° C., aeration of 0.5 vvm and rotating the stirrer provided with the fermentation tank at 150 rpm, and during culturing, the pH was controlled to pH 7.6 with aqueous sodium hydroxide solution having a concentration of 4 mol/l and sulfuric acid having a concentration of 4 mol/l.

Culturing was carried out for 5 days, and the numbers of sporangia and microbial cells per unit volume in the liquid cultures were measured by direct microscopic examination followed by calculation of the sporangia formation rates. Those results are shown in Table 13.

TABLE 13

| Medium Name | L-proline concentration in liquid culture (wt %) | Ratio of L-proline to total amino acids (wt %) | No. of microbial cells (cells/ml) | No. of sporangia (sporangia/ml) | Sporangia formation rate (%) |
|---|---|---|---|---|---|
| E-1 | 0.504 | 48.154 | $1.4 \times 10^9$ | $2.0 \times 10^8$ | 14.3 |
| E-2 | 0.504 | 48.154 | $1.6 \times 10^9$ | $4.8 \times 10^8$ | 29.3 |
| F | 0.004 | 0.680 | $1.0 \times 10^9$ | $<1.0 \times 10^4$ | 0 |

One spore and one parasporal body were contained in the sporangia obtained in Examples 5 and 6 using media (E-1) and (E-2). In addition, as is clear from the results shown in Table 13, the number of sporangia containing spores and parasporal bodies per unit volume of medium was able to be further increased by adding sodium pyruvate and controlling the pH.

Biological Test Example 1

A test was conducted on the growth inhibitory effects on larva of *Scarabaeidae* insects of sporangia obtained by the production process of the present invention.

Sporangia of *Bacillus popilliae Semadara* acquired in medium using liquid medium (A) of Example 1 were suspended in distilled water to $2 \times 10^8$ sporangia/ml to prepare suspension (I). Moreover, a suspension containing said sporangia was treated with a French press to separate and remove the spores and parasporal bodies from the sporangia. The separated spores were suspended in distilled water to $2 \times 10^8$ spores/ml to prepare suspension (II). In addition, the separated parasporal bodies were suspended in distilled water to $2 \times 10^8$ parasporal bodies/ml to prepare suspension (III).

Eighty plastic cups were prepared having a diameter of 6 cm and filled with about 20 g each of leaf mold.

(i) Suspension (I) containing sporangia containing spores and parasporal bodies was sprayed onto 20 plastic cups so that the number of sporangia was $2 \times 10^8$ sporangia/cup.

(ii) Suspension (II) containing spores only was sprayed onto 20 plastic cups so that the number of spores was $2 \times 10^8$ spores/cup.

(iii) Suspension (III) containing parasporal bodies only was sprayed onto 20 plastic cups so that the number of parasporal bodies was $2 \times 10^8$ parasporal bodies/cup.

(iv) Nothing was sprayed onto the remaining 20 cups and these cups were used as a control test.

One second instar larva each of *Anomala cuprea* was placed in each cup and bred for 30 days in an incubator at 25° C. followed by measuring the mortality rates and average body weight increase of the surviving larva over time. The cumulative mortality rates are shown in Table 14, while the results for growth inhibitory effects are shown in FIG. 3.

TABLE 14

| Test Group | Cumulative Mortality Rates (%) | | |
| --- | --- | --- | --- |
| | Day 11 | Day 23 | Day 30 |
| (i) | 20 | 40 | 45 |
| (ii) | 0 | 5 | 10 |
| (iii) | 15 | 20 | 25 |
| (iv) Control | 0 | 0 | 0 |

Figure 3:
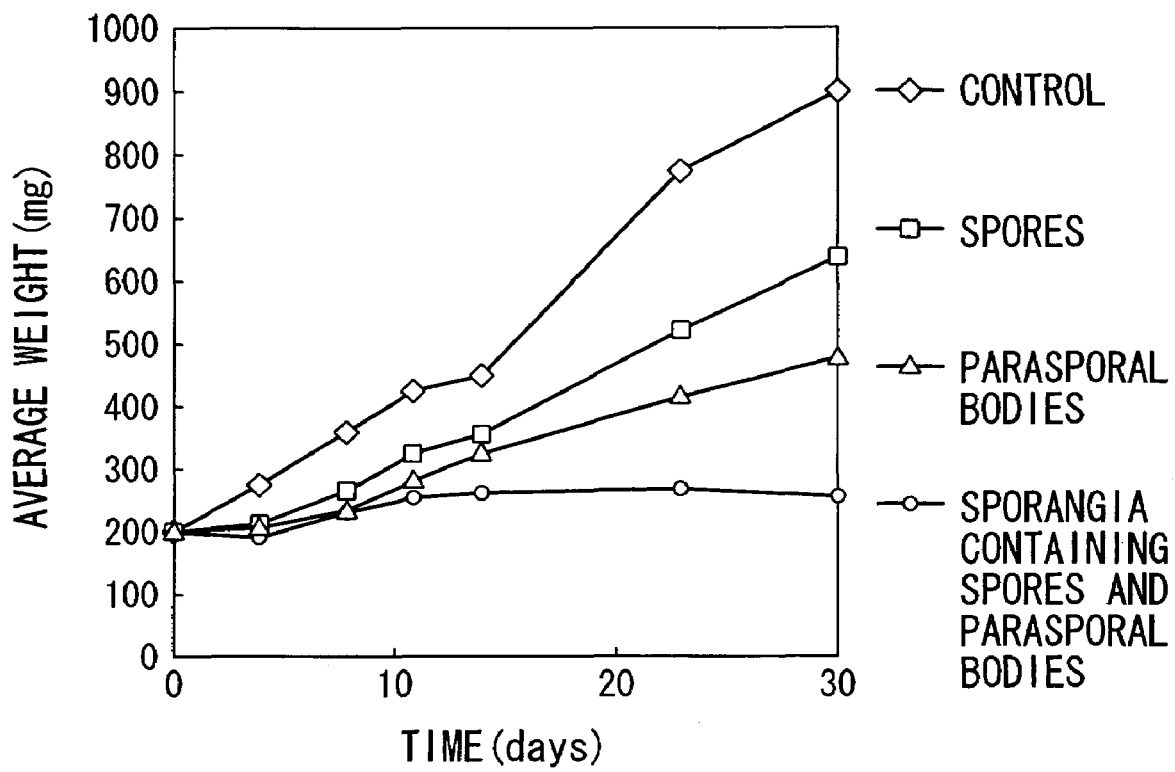
FIG. 3 is a graph showing the growth inhibitory effects on *Anomala cuprea* in Biological Test Example 1.

As is clear from Table 14 and FIG. 3, sporangium containing both spores and parasporal bodies were confirmed to demonstrate superior insecticidal and larva growth inhibitory effects on the larva of *Scarabaeidae* insects as compared with the case of spores alone and the case of parasporal bodies alone.

Biological Test Example 2

A test was conducted of the insecticidal activity on *Scarabaeidae* insects by sporangia obtained according to the production process (liquid culturing) of the present invention.

Approximately 20 g of leaf mold were placed in 60 plastic cups having a diameter of 6 cm, and a sporangia liquid containing sporangia of (i) or (ii) below was sprayed onto 20 cups each so that the number of said sporangia was $1 \times 10^9$ sporangia/cup.

However, the sprayed sporangia liquids used in this test consisted of (i) sporangia of *Bacillus popilliae Semadara* containing spores and parasporal bodies acquired by culturing using liquid medium (A) of Example 1, and (ii) sporangia of *Bacillus popilliae* var. *popilliae Mame* acquired by culturing in medium using liquid medium (A) of Example 1.

In addition, nothing was sprayed onto the remaining 20 cups and these cups were used as a control test. One second instar larva each of *Anomala cuprea* was placed in each cup and bred for 40 days in an incubator at 25° C. followed by investigating the number of insects that died over time to determine the cumulative mortality rates (%). Those results are shown in Table 15.

TABLE 15

| Test Group | Cumulative Mortality Rates (%) | | | |
| --- | --- | --- | --- | --- |
| | Day 10 | Day 20 | Day 30 | Day 40 |
| (i) | 25 | 40 | 90 | 100 |
| (ii) | 15 | 40 | 75 | 80 |
| Control | 0 | 0 | 0 | 0 |

Based on the results shown in Table 15, mortality rates of 80–100% were observed on day 40. Namely, sporangia containing spores and parasporal bodies of *Bacillus popilliae* were confirmed to have superior insecticidal and larval growth inhibitory effects on larva of *Scarabaeidae* insects.

Biological Test Example 3

A test was conducted of the insecticidal activity on *Scarabaeidae* insects by sporangia obtained according to the production process (liquid culturing) of the present invention. Sporangia of *Bacillus popilliae Semadara* containing spores and parasporal bodies obtained by culturing in liquid medium (E-2) shown in Example 6 were suspended in distilled water to $1 \times 10^9$ sporangia/ml to prepare a sporangia liquid.

Approximately 20 g of leaf mold each were placed in 40 plastic cups having a diameter of 6 cm. The sporangia liquid was sprayed onto 20 of the cups so that the number of sporangia was $1 \times 10^9$ sporangia/cup. Sporangia liquid was not sprayed onto the remaining 20 cups and these cups were used as a control test. One second instar larva each of *Anomala cuprea* was placed in each cup and bred for 40 days in an incubator at 25° C. followed by investigating the number of insects that died over time to determine the cumulative mortality rates (%). Those results are shown in Table 16.

TABLE 16

| Test Group | Cumulative Mortality Rates (%) | | | |
| --- | --- | --- | --- | --- |
| | Day 10 | Day 20 | Day 30 | Day 40 |
| Control | 0 | 0 | 0 | 0 |
| Sporangia addition | 10 | 40 | 90 | 100 |

Based on the results shown in Table 16, the resulting sporangia demonstrated insecticidal activity, with all of the larva having died by day 40. Namely, sporangia of *Bacillus popilliae Semadara* containing spores and parasporal bodies obtained in Example 6 were confirmed to have superior insecticidal and larval growth inhibitory effects on larva of *Scarabaeidae* insects.

What is claimed is:

1. A process for producing sporangia of *Bacillus popilliae* containing spores and parasporal bodies, comprising the step of:

culturing *Bacillus popilliae* in a liquid medium containing an adsorbent and 0.1–0.7% by weight of proline.

2. A process for producing sporangia of *Bacillus popilliae* according to claim 1, wherein the ratio of proline to total amino acids contained in the liquid medium is within the range of 10 to 65% by weight.

3. A process for producing sporangia of *Bacillus popilliae* according to claim 1, wherein the ratio of adsorbent contained in the liquid medium is 0.05–5% by weight.

4. A process for producing sporangia of *Bacillus popilliae* according to claim 1, wherein the liquid medium additionally contains pyruvic acid.

5. A process for producing sporangia of *Bacillus popilliae* according to claim 4, wherein the ratio of pyruvic acid in the liquid medium is within the range of 0.01 to 0.5% by weight.

6. A process for producing sporangia of *Bacillus popilliae* according to claim 1, 3 or 4, wherein the microorganism belonging to *Bacillus popilliae* is *Bacillus popilliae* Semadara, *Bacillus popilliae* var. *popilliae* Mame, *Bacillus popilliae* var. *popilliae* Hime or *Bacillus popilliae* var. *popilliae* Sakura.

* * * * *